United States Patent

Pisson et al.

[11] Patent Number: 5,882,633
[45] Date of Patent: Mar. 16, 1999

[54] COMPOSITIONS COMPRISING A DIBENZOYLMETHANE DERIVATIVE, A 1,3, 5-TRIAZINE DERIVATIVE AND AN AMIDE COMPOUND, AND METHODS OF USE THEREFOR

[75] Inventors: Anne-Marie Pisson, Brunoy; Delphine Allard, Colombes; Didier Candau, Bievres, all of France

[73] Assignee: Societe L'Oreal S.A., Paris, France

[21] Appl. No.: 992,476

[22] Filed: Dec. 17, 1997

[30] Foreign Application Priority Data

Dec. 17, 1996 [FR] France .................................. 96 15513

[51] Int. Cl.[6] ............................ A61K 7/42; A61K 31/53; A61K 31/12; A61K 7/00
[52] U.S. Cl. ............................. 424/59; 424/60; 424/400; 424/401; 514/242; 514/679
[58] Field of Search ................................ 424/59, 60, 400, 424/401; 514/242, 679

[56] References Cited

FOREIGN PATENT DOCUMENTS

| 0457687 | 11/1991 | European Pat. Off. . |
| 0517104 | 12/1992 | European Pat. Off. . |
| 0689828 | 1/1996 | European Pat. Off. . |
| 0717982 | 6/1996 | European Pat. Off. . |

*Primary Examiner*—Shelley A. Dodson
*Attorney, Agent, or Firm*—Burns, Doane, Swecker & Mathis, L.L.P.

[57] ABSTRACT

The present invention relates to novel cosmetic and/or dermatological compositions comprising, in a cosmetically and/or dermatologically acceptable support, i) a dibenzoylmethane derivative, in particular 4-tert-butyl-4'-methoxydibenzoylmethane, ii) at least one specific 1,3,5-triazine derivative, and iii) at least one amide compound. These compositions are particularly photostable. The invention also relates to the use of these compositions in the cosmetic and/or dermatological fields, in particular, as a sunscreen.

24 Claims, No Drawings

COMPOSITIONS COMPRISING A DIBENZOYLMETHANE DERIVATIVE, A 1,3, 5-TRIAZINE DERIVATIVE AND AN AMIDE COMPOUND, AND METHODS OF USE THEREFOR

CROSS-REFERENCE TO COMPANION APPLICATIONS

Our copending applications Ser. No. 08/992,475, and Serial No. 08/992,477, both filed concurrently herewith and assigned to the Assignee hereof.

BACKGROUND OF THE INVENTION

1. Technical Field of the Invention

The present invention relates to novel cosmetic and/or dermatological compositions (referred to herein below as sunscreen compositions) intended for protecting the skin and/or the hair against the deleterious effects of UV radiation, in particular, solar radiation. More specifically, the invention relates to novel cosmetic and/or dermatological compositions with enhanced photostability and comprising, in a cosmetically and/or dermatologically acceptable support or carrier, a combination of at least three specific UV-screening agents.

This invention also relates to the use of photoprotecting compositions in the cosmetic and/or dermatological fields.

2. Description of the Prior Art

It is known to this art that light radiation of wavelengths of from 280 nm to 400 nm promotes tanning of the human epidermis, and that light radiation with wavelengths more particularly of from 280 to 320 nm, i.e., UV-B irradiation, causes skin burning and erythema which can impair the development of a natural tan. For these reasons, as well as for aesthetic reasons, there is an increasingly demand for a means of controlling this natural tanning in order to thereby control the color of the skin. This UV-B radiation must be screened from the skin.

It is also known to this art that UV-A radiation of wavelengths of from 320 to 400 nm, which tan the skin, also adversely affects it, especially in the case of sensitive skin or skin which is continually exposed to solar radiation. UV-A rays especially cause a loss in the elasticity of the skin and the appearance of wrinkles, thereby promoting premature skin aging. Such irradiation promotes triggering of the erythemal reaction or amplifies this reaction in certain individuals. They may even be the cause of phototoxic or photoallergic reactions. Thus, for aesthetic and cosmetic reasons, such as conservation of the natural elasticity of the skin, for example, an ever-increasing number of people wish to control the effect of UV-A rays on their skin, it is therefore desirable also to screen out UV-A radiation.

Thus, with the aim of providing protection for the skin and the hair against UV radiation as a whole, this protection being as full and as effective as possible, combinations of screening agents which are active in the UV-A range and of screening agents which are active in the UV-B range are generally used in the manufacture of sunscreen compositions.

In this respect, a particularly advantageous family of UV-A screening agents currently include the dibenzoylmethane derivatives and, in particular, 4-(tert-butyl)-4'-methoxydibenzoylmethane, which effectively have a high intrinsic power of absorption. These dibenzoylmethane derivatives, which are now products that are well known in the art as sunscreen agents that are active in the UV-A range, are described in particular in FR-A-2,326,405 and FR-A-2, 440,933, as well as in EP-A-0,114,607. 4-(Tert-butyl)-4'-methoxydibenzoylmethane is currently sold under the trademark "Parsol 1789" by Givaudan.

Similarly, 1,3,5-triazine derivatives and, in particular, 2,4,6-tris[p-(2'-ethylhexyl-1'-oxycarbonyl)anilino]-1,3,5-triazine, sold under the trademark "Uvinul T 150" by BASF, have a high power for absorbing UV-B radiation. It would thus be very advantageous to be able to use these compounds in combination with 4-tert-butyl-4'-methoxydibenzoylmethane for the purpose of obtaining products offering wide and effective protection throughout the full UV radiation range.

However, the inventors have observed that when these 1,3,5-triazine derivatives are in the presence of dibenzoylmethane derivatives, in particular, 4-tert-butyl-4'-methoxydibenzoylmethane, and under UV irradiation, they have the disadvantage of undergoing considerable chemical degradation. Under these conditions, the combination of two screening agents no longer allows broad, prolonged sunscreen protection for the skin and the hair.

SUMMARY OF THE INVENTION

After considerable research conducted in the abovementioned field of photoprotection, the inventors have unexpectedly and surprisingly discovered that the introduction of an amide compound into a composition containing a dibenzoylmethane derivative, in particular, 4-tert-butyl-4'-methoxydibenzoylmethane, in combination with at least one 1,3,5-triazine derivative, and in particular, with 2,4,6-tris[p-(2'-ethylhexyl-1'-oxycarbonyl)anilino]-1,3,5-triazine, allows the photostability of the 1,3,5-triazine derivative in the composition, and thus the overall efficacy of the composition, to be enhanced quite substantially.

The subject of the present invention is thus novel cosmetic and/or dermatological compositions comprising, in a cosmetically and/or dermatologically acceptable support or carrier:

(i) at least one 1,3,5-triazine derivative corresponding to formula (I) below:

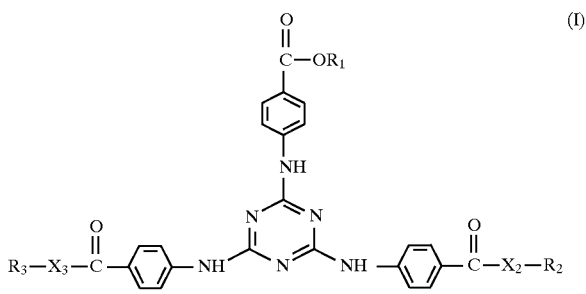

wherein the radicals:
  $X_2$ and $X_3$, which may be identical or different, represent oxygen or an —NH— radical;
  $R_1$, $R_2$ and $R_3$, which may be identical or different, are each a hydrogen; an alkali metal; an ammonium radical optionally substituted with one or more alkyl or hydroxyalkyl radicals; a linear or branched $C_1$–$C_{18}$ alkyl radical; a $C_5$–$C_{12}$ cycloalkyl radical optionally substituted with one or more $C_1$–$C_4$ alkyl radicals; a polyoxyethylenated radical comprising from 1 to 6 ethylene oxide units and whose terminal OH group is methylated; a radical of formulae (II), (III) or (IV) below:

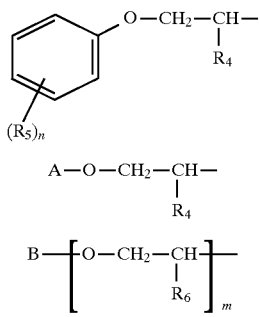

wherein:
- $R_4$ is hydrogen or a methyl radical;
- $R_5$ is a $C_1$–$C_9$ alkyl radical;
- n is an integer ranging from 0 to 3;
- m is an integer ranging from 1 to 10;
- A is a $C_4$–$C_8$ alkyl radical or a $C_5$–$C_8$ cycloalkyl radical;
- B is a linear or branched $C_1$–$C_8$ alkyl radical; a $C_5$–$C_8$ cycloalkyl radical; or an aryl radical optionally substituted with one or more $C_1$–$C_4$ alkyl radicals; and
- $R_6$ is hydrogen or a methyl radical, (ii) at least one dibenzoylmethane derivative corresponding to formula (V) below:

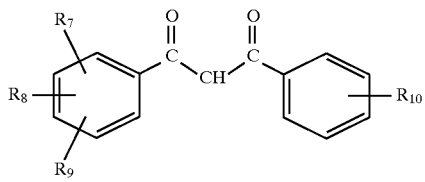

wherein $R_7$, $R_8$, $R_9$ and $R_{10}$, which may be identical or different, independently represent hydrogen or a hydroxyl radical or a linear or branched $C_1$–$C_8$ alkyl radical or a linear or branched $C_1$–$C_8$ alkoxy radical, and (iii) at least one amide compound.

Thus, according to the present invention, cosmetic and/or dermatological compositions containing a dibenzoylmethane derivative, in particular, 4-tert-butyl-4'-methoxydibenzoylmethane, in combination with at least one 1,3,5-triazine derivative, can be prepared, wherein the concentration of 1,3,5-triazine derivative in the composition remains relatively constant even if these compositions are exposed to light.

DETAILED DESCRIPTION OF BEST MODE AND SPECIFIC/PREFERRED EMBODIMENTS OF THE INVENTION

The present invention features the subject compounds formulated into cosmetic and/or dermatological compositions containing a dibenzoylmethane derivative as defined above, in particular, 4-tert-butyl-4'-methoxydibenzoylmethane, in combination with at least one 1,3,5-triazine derivative as defined above, in order to enhance the stability to UV radiation (photostability) of the 1,3,5-triazine derivative in the compositions.

The subject of the present invention is also a process for enhancing the stability of a composition to UV radiation (photostability), and thus the efficacy, of a cosmetic and/or dermatological composition comprising a dibenzoylmethane derivative as defined above, in particular, 4-tert-butyl-4'-methoxydibenzoylmethane, and a 1,3,5-triazine derivative as defined above, in particular, 2,4,6-tris[p-(2'-ethylhexyl-1'-oxycarbonyl)anilino]-1,3,5-triazine. The process comprises introducing an effective amount of an amide compound into the composition.

By the expression "effective amount of an amide compound" is intended an amount which is sufficient to obtain a noticeable and significant improvement in the photostability of the dibenzoylmethane derivative(s) contained in the composition. This minimum amount of stabilizer to be used, which can vary depending on the nature of the cosmetically acceptable support selected for the composition, can readily be determined by means of a standard test of measuring the photostability, such as that given in the examples below.

Other characteristics, aspects and advantages of the present invention will become apparent on reading the detailed description which follows.

A first compound in the compositions envisaged by the present invention is a particular 1,3,5-triazine derivative. Thus, the 1,3,5-triazine derivatives which can be used in the context of the present invention comprise those corresponding to formula (I) below:

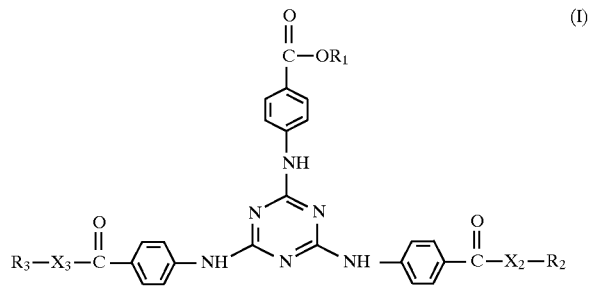

wherein:
- $X_2$ and $X_3$, which may be identical or different, represent oxygen or an —NH— radical;
- $R_1$, $R_2$ and $R_3$, which may be identical or different are each a hydrogen; an alkali metal; an ammonium radical optionally substituted with one or more alkyl or hydroxyalkyl radicals; a linear or branched $C_1$–$C_8$ alkyl radical; a $C_5$–$C_{12}$ cycloalkyl radical optionally substituted with one or more $C_1$–$C_4$ alkyl radicals; a polyoxyethylenated radical comprising from 1 to 6 ethylene oxide units and whose terminal OH group is methylated; a radical of formula (II), (III) or (IV) below:

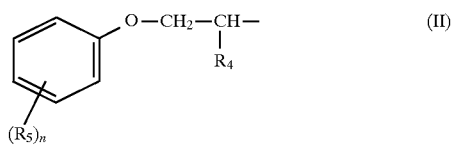

wherein:
- $R_4$ is hydrogen or a methyl radical;
- $R_5$ is a $C_1$–$C_9$ alkyl radical;
- n is an integer ranging from 0 to 3;
- m is an integer ranging from 1 to 10;
- A is a $C_4$–$C_8$ alkyl radical or a $C_5$–$C_8$ cycloalkyl radical;

B is a linear or branched $C_1-C_8$ alkyl radical; a $C_5-C_8$ cycloalkyl radical; or an aryl radical optionally substituted with one or more $C_1-C_4$ alkyl radicals;

$R_6$ is hydrogen or a methyl radical.

Obviously, in the above definition, when $X_2$ and/or $X_3$ represent an —NH— radical, then the corresponding radical (s) $R_2$ and/or $R_3$ are other than an alkali metal or an ammonium radical.

The preferred 1,3,5-triazine derivatives are those described, in particular, in EP-A-0,517,104, namely, 1,3,5-triazines corresponding to formula (I) above and having all of the following characteristics:

$X_2$ and $X_3$ are identical and represent oxygen;

$R_1$ is a $C_5-C_{12}$ cycloalkyl radical optionally substituted with one or more $C_1-C_4$ alkyl radicals; a radical of formulae (II), (III) or (IV) above wherein:

B is a $C_1-C_4$ alkyl radical;

is a methyl radical;

$R_2$ and $R_3$, which may be identical or different, are each a hydrogen; an alkali metal; an ammonium radical optionally substituted with one or more alkyl or hydroxyalkyl radicals; a linear or branched $C_1-C_{18}$ alkyl radical; a $C_5-C_{12}$ cycloalkyl radical optionally substituted with one or more $C_1-C_4$ alkyl radicals; or a radical of formulae (II), (III) or (IV) above wherein:

B is a $C_1-C_4$ alkyl radical;

$R_6$ is a methyl radical.

A second preferred set of 1,3,5-triazine derivatives according to the invention are those described, in particular, in EP-A-0,570,838, namely, 1,3,5-triazines corresponding to formula (I) and having all of the following characteristics:

$X_3$ is an —NH— radical;

$R_3$ is a linear or branched $C_1-C_{18}$ alkyl radical; or a $C_5-C_{12}$ cycloalkyl radical optionally substituted with one or more $C_1-C_4$ alkyl radicals;

$R_1$ is hydrogen; an alkali metal; an ammonium radical; a radical of formula (IV); a linear or branched $C_1-C_{18}$ alkyl radical; or a $C_5-C_{12}$ cycloalkyl radical optionally substituted with one or more $C_1-C_4$ alkyl radicals;

if $X_2$ is an —NH— radical, then $R_2$ is a linear or branched $C_1-C_{18}$ alkyl radical; or a $C_5-C_{12}$ cycloalkyl radical optionally substituted with one or more $C_1-C_4$ alkyl radicals;

if $X_2$ is oxygen, then $R_2$ is hydrogen; an alkali metal; an ammonium radical; a radical of formula (IV); a linear or branched $C_1-C_{18}$ alkyl radical; or a $C_5-C_{12}$ cycloalkyl radical optionally substituted with one or more $C_1-C_4$ alkyl radicals. A particularly preferred 1,3,5-triazine of the second preferred set of compounds is that corresponding to the following formula:

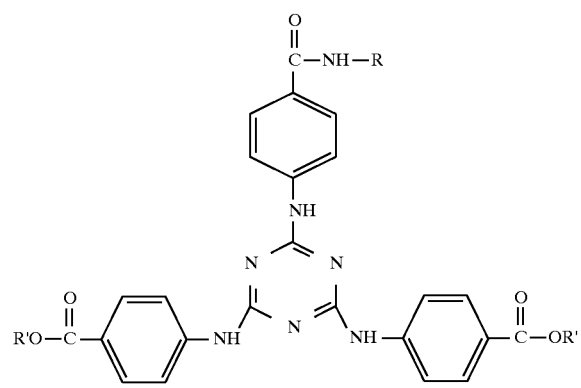

wherein R' represents a 2-ethylhexyl radical and R represents a tert-butyl radical.

A third preferred set of compounds is that described, in particular, in U.S. Pat. No. 4,724,137, namely, 1,3,5-triazines corresponding to formula (I) and having the following characteristics:

$X_2$ and $X_3$ are identical and represent oxygen;

$R_1$, $R_2$ and $R_3$ are identical and represent a $C_6-C_{12}$ alkyl radical or a polyoxyethylenated radical comprising from 1 to 6 ethylene oxide units and in which the terminal OH group is methylated.

A particularly preferred 1,3,5-triazine of this third preferred set is 2,4,6-tris[p-(2'-ethylhexyl-1'-oxycarbonyl) anilino]-1,3,5-triazine, which is a sunscreen which is known in the art. It is active in the UV-B range, is in solid form and is sold, in particular, under the trademark "Uvinul T 150" by BASF. This compound corresponds to the following formula:

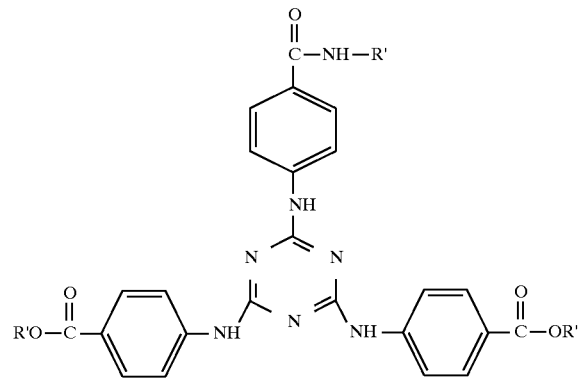

wherein R' represents a 2-ethylhexyl radical.

The 1,3,5-triazine derivative(s) is/are generally present in the compositions of the present invention in a proportion which may range from 0.5% to 20%, preferably from 1% to 10%, by weight, relative to the total weight of the composition.

As indicated above, the dibenzoylmethane derivatives which can be used according to the present invention are those corresponding to formula (V) below:

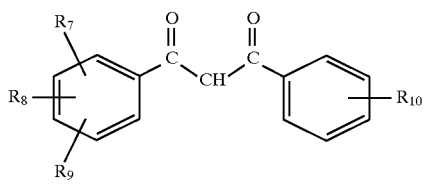

wherein $R_7$, $R_8$, $R_9$ and $R_{10}$, which may be identical or different, independently represent hydrogen or a hydroxyl radical or a linear or branched $C_1$–$C_8$ alkyl radical or a linear or branched $C_1$–$C_8$ alkoxy radical.

According to the present invention, one or more dibenzoylmethane derivatives can, of course, be used.

Among the dibenzoylmethane derivatives which can be used according to the present invention, mention may be made in particular, in a non-limiting manner, of:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4-tert-butyl-4'-methoxydibenzoylmethane,
2-methyl-5-isopropyl-4'-methoxy-dibenzoylmethane,
2-methyl-5-tert-butyl-4'-methoxy-dibenzoylmethane,
2,4-dimethyl-4'-methoxydibenzoylmethane,
2,6-dimethyl-4-tert-butyl-4'-methoxy-dibenzoylmethane, and
4,4'-dimethoxydibenzoylmethane.

These products are already well known per se and are described in particular in the abovementioned documents FR-A-2,326,405, FR-A-2,440,933 and EP-A-0,114,607.

Among the dibenzoylmethane derivatives, the preferred compound is 4-(tert-buty)-4'-methoxy-dibenzoylmethane. That compound is sold under the trademark "Parsol 1789" by Givaudan. That compound/sunscreen corresponds to the following formula:

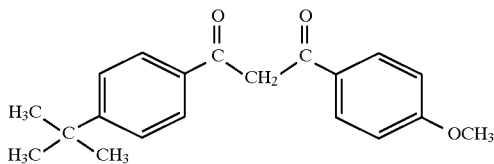

Another preferred dibenzoylmethane derivative is 4-isopropyldibenzoylmethane. That sunscreen is sold under the trademark "Eusolex 8020" by Merck, and corresponds to the following formula:

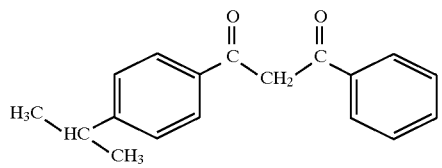

The dibenzoylmethane derivatives can be present in the compositions of the present invention in an amount ranging from 0.2% to 15% by weight relative to the total weight of the composition, preferably, the amount ranges from 0.2% to 10%.

A third essential compound of the composition of the present invention is a compound from the amide family of compounds.

For the purposes of the present invention, the term "amide compound" refers to any compound having in its chemical structure at least one amide group (or function)

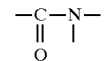

In a preferred embodiment of the present invention, the amide compounds correspond to formula (VI) below:

wherein the radicals $R_{11}$, $R_{12}$ and $R_{13}$, which may be identical or different, independently represent hydrogen or monovalent, saturated or unsaturated, aliphatic, cycloaliphatic or cyclic, optionally functionalized hydrocarbon radicals containing from 1 to 30 carbon atoms, preferably from 1 to 22 carbon atoms, inclusive, it being understood that, in this formula, the radical $R_{11}$ can form, with the radical $R_{12}$ or with the radical $R_{13}$, a ring containing from 5 to 18 carbon atoms, inclusively, and that the radicals $R_{12}$ and $R_{13}$ can together form a ring containing from 5 to 18 carbon atoms, inclusive.

As examples of saturated aliphatic hydrocarbon radicals, mention may be made in particular of linear or branched, substituted or unsubstituted, $C_1$–$C_{30}$, preferably $C_1$–$C_{22}$, alkyl radicals and, in particular, the methyl, ethyl, n-propyl, isopropyl, n-butyl, isobutyl, tert-butyl, pentyl, n-amyl, isoamyl, neopentyl, n-hexyl, n-heptyl, n-octyl, 2-ethylhexyl, tert-octyl, decyl, lauryl and octadecyl radicals.

Example of saturated cyclic hydrocarbon radicals, include, in particular, the cyclopentyl and cyclohexyl radicals, optionally substituted, in particular, with alkyl radicals.

Examples of unsaturated aliphatic hydrocarbon radicals, include, in particular, the linear or branched, substituted or unsubstituted, $C_2$–$C_{30}$, preferably $C_2$–$C_{22}$, alkenyl or alkynyl radicals and, in particular, the vinyl, allyl, oleyl and linoleyl radicals.

Examples of unsaturated cyclic hydrocarbon radicals, include, in particular, aryl radicals such as phenyl and naphthyl, optionally substituted, in particular, with alkyl radicals, such as, for example, the tolyl radical, and by way of example of unsaturated cycloaliphatic radicals, mention may be made more particularly of the benzyl and phenylethyl radicals.

The term "functionalized radicals" is preferably intended to refer to radicals containing in their chemical structure, both in the main chain and on a side chain, one or more functional groups of the ester, ether, alcohol, amine, amide and ketone type. Esters are the preferred functionalized radical.

Among the amide compounds of formula (VI) which are suitable in the practice of the present invention, it is more particularly preferred to use compounds having at least one, and even more preferably all, of the following characteristics:

the amide compound is an N-substituted amide, and even more preferably N,N-disubstituted, $R_{11}$ is a linear or branched, preferably $C_1$–$C_{22}$ and even more preferably $C_1$–$C_{12}$, alkyl radical, or alternatively a phenyl radical which is itself optionally substituted with one or more linear or branched $C_1$–$C_{12}$ alkyl radicals, $R_{12}$ is a linear or branched, preferably $C_1$–$C_{22}$ and even more preferably $C_1$–$C_{12}$, alkyl radical, $R_{13}$ is a linear or branched alkyl radical having the same definition as $R_{12}$, or alternatively represents a monovalent radical with an ester function corresponding to formula (VII) below:

(VII)

wherein $R_{14}$ and $R_{15}$, which may be identical or different, represent two hydrocarbon radicals, preferably of the alkyl type, containing from 1 to 12 carbon atoms, preferably from 1 to 8 carbon atoms.

According to a specific embodiment of the present invention, the amide compounds defined above are fatty substances that are liquid at room temperature. Preferably, they are oils which have good solubility in the fatty phases usually used for the preparation of cosmetically acceptable supports or carriers.

Example of specific amide oils which have entirely remarkable properties in the photo-stabilization of 1,3,5-triazine derivatives, in particular, 2,4,6-tris[p-(2'-ethylhexyl-1'-oxycarbonyl)-anilino]-1,3,5-triazine, include:

N,N-diethylmethylbenzamides of formula (1) below:

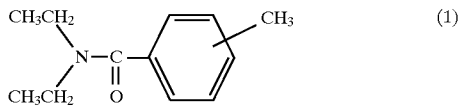

(1)

including N,N-diethyl-3-methylbenzamide, ethyl N-butyl-N-acetylaminopropionate of formula (2) below:

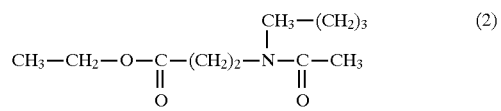

(2)

In general, the amide compound(s) can be present in the compositions in accordance with the present invention in an amount ranging from 0.01% to 50% by weight, and preferably from 0.1% to 30% by weight, relative to the total weight of the composition.

Thus, when a sufficient amount of an amide compound is added to a sunscreen composition containing a dibenzoylmethane derivative, in particular, 4-tert-butyl-4'-methoxydibenzoylmethane, and a 1,3,5-triazine derivative as defined above, an increase in the stability of the 1,3,5-triazine derivative to light is observed, and thus an increase in the efficacy of the sunscreen composition over time.

The cosmetic and/or dermatological compositions disclosed by the present invention can, of course, contain one or more additional hydrophilic or lipophilic UV-A- and/or UV-B-active sunscreens (absorbers) other than, of course, the three sunscreen compounds identified above. These additional sunscreen agents are advantageously selected, in particular, from among the cinnamic derivatives, salicylic derivatives, benzylidene camphor derivatives, benzimidazole derivatives, triazine derivatives other than those mentioned above, benzophenone derivatives, β,β-diphenylacrylate derivatives, p-aminobenzoic acid derivatives, and the screening polymers and screening silicones described in WO-93/04665. Other examples of organic screening agents are provided in EP-A-0,487,404.

The compositions according to the invention can also contain agents for the artificial tanning and/or bronzing of the skin (self-tanning agents), such as, for example, dihydroxyacetone (DHA).

The cosmetic and/or dermatological compositions according to the present invention can also contain pigments or nanopigments (average size of the primary particles: generally range from 5 nm to 100 nm, preferably from 10 to 50 nm) of coated or uncoated metal oxides such as, for example, nanopigments of titanium dioxide (amorphous or crystallized in rutile and/or anatase form), iron oxide, zinc oxide, zirconium oxide or cerium oxide, which are all photoprotective agents which are well known to this art and act by physically blocking (reflection and/or diffusion) UV radiation. Standard coating agents are alumina and/or aluminum stearate. Such coated or uncoated metal oxide nanopigments are described, in particular, in EP-A-0,518,772 and EP-A-0,518,773.

The compositions in accordance with the present invention may also comprise typical additives and adjuvants in the cosmetics field, such as fatty substances, organic solvents, ionic or nonionic thickeners, softeners, antioxidants, anti-free-radical agents, opacifiers, stabilizers, emollients, silicones, α-hydroxy acids, antifoaming agents, moisturizers, vitamins, fragrances, preservatives, surfactants, fillers, sequestering agents, polymers, propellants, basifying or acidifying agents, dyes or any other ingredients usually used in the cosmetic and/or dermatological field, in particular, for the formulation of sunscreen compositions in the form of emulsions.

Exemplary fatty substances include an oil or a wax or mixtures thereof. By the term "oil" is intended a compound which is liquid at room temperature. By the term "wax" is intended a compound which is solid or substantially solid at room temperature, and whose melting point is generally above 35° C.

Exemplary oils include mineral oils (petroleum jelly); plant oils (sweet almond oil, macadamia oil, grapeseed oil, jojoba oil); synthetic oils such as perhydrosqualene, fatty alcohols, fatty acids or fatty esters (such as C12–C15 alkyl benzoates sold under the trademark "Finsolv TN" by Finetex, octyl palmitate, isopropyl lanolate, triglycerides including those of capric/caprylic acid), oxyethylenated or oxypropylenated fatty esters and fatty ethers; silicone oils (cyclomethicone, polydimethylsiloxanes, or PDMS) or fluoro oils; polyalkylenes.

Exemplary waxy compounds include paraffin, carnauba wax, beeswax and hydrogenated castor oil.

Exemplary organic solvents include lower alcohols and polyols.

The thickeners can be chosen in particular from crosslinked polyacrylic acids and modified or unmodified guar gums and celluloses, such as hydroxypropyl guar gum, methylhydroxyethylcellulose and hydroxypropylmethylcellulose.

Needless to say, a person skilled in the art will take care to select the optional additional compound(s) mentioned above (in particular, the additional screening agents) and/or the amounts thereof, such that the advantageous properties intrinsically associated with the ternary combination in accordance with the invention are not, or are not substantially, adversely affected by the additional compounds which may be present and therefore the good cosmetic properties of the composition will be retained.

The compositions according to the invention can be prepared according to techniques which are well known to those skilled in the art, in particular, those intended for the preparation of oil-in-water or water-in-oil type emulsions.

The composition of the present invention can be, in particular, in the form of a simple or complex emulsion (O/W, W/O, O/W/O or W/O/W) such as a cream, a milk, or in the form of a gel or a cream gel, a powder or a solid stick and can optionally be packaged as an aerosol or in the form of a foam or a spray.

Preferably, the compositions according to the invention are in the form of an oil-in-water emulsion.

The aqueous phase of the emulsion can comprise a nonionic vesicle dispersion prepared according to known processes (Bangham, Standish and Watkins, *J. Mol. Biol.,* 13, 238 (1965), FR 2,315,991 and FR 2,416,008).

The cosmetic and/or dermatological composition of the invention can be used as a composition for protecting the human epidermis or the hair against ultraviolet rays, as a sunscreen or as a makeup product.

When the cosmetic composition according to the invention is used to protect the human epidermis against UV rays, or as a sunscreen, it can be in the form of a suspension or a dispersion in solvents or fatty substances, in the form of a nonionic vesicle dispersion or alternatively in the form of an emulsion, preferably an oil-in-water emulsion, such as a cream or a milk, or in the form of ointments, gels, cream gels, solid pencils, sticks, aerosol foams or sprays.

When the cosmetic compositions according to the present invention are used for protecting the hair, they may be in the form of a shampoo, a lotion, a gel, an emulsion, a nonionic vesicle dispersion or a lacquer for the hair and can constitute, for example, a composition which is applied to the hair and rinsed out with water, also referred to as a rinse, to be applied before or after shampooing, before or after dyeing or bleaching, before, during or after permanent-waving or straightening of the hair, a styling or treating lotion or gel, a blow-drying or hairsetting lotion or gel, or a permanent-waving, straightening, dyeing or bleaching composition for the hair.

When the compositions are formulated as a makeup product for the eyelashes, the eyebrows or the skin, such as epidermal treatment creams, foundations, tubes of lipstick, eyeshadows, blushers, mascaras or eyeliners, they may be in solid or pasty, anhydrous or aqueous form, such as oil-in-water or water-in-oil emulsions, nonionic vesicular dispersions or suspensions.

As a guide for the sunscreen formulations having an oil-in-water emulsion support, the aqueous phase (comprising in particular the hydrophilic screening agents) generally represents from 50 to 95% by weight, preferably from 70 to 90% by weight, relative to the formulation as a whole, the oil phase (comprising in particular the lipophilic screening agents) represents from 5 to 50% by weight, preferably from 10 to 30% by weight, relative to the formulation as a whole, and the (co)emulsifier(s) represent (s) from 0.5 to 20% by weight, preferably from 2 to 10% by weight, relative to the formulation as a whole.

In order to further illustrate the present invention and the advantages thereof, the following specific examples are given, it being understood that same are intended only as illustrative and in nowise limitative.

EXAMPLE

Three oil-in-water emulsions A, B and C were prepared, in which the common support or base has the following composition (the amounts are expressed as a % by weight relative to the total weight of the composition):

| | |
|---|---|
| glyceryl monostearate/polyethylene glycol stearate mixture (100 EO) sold under the | 2% |

-continued

| | | |
|---|---|---|
| trademark "Arlacel 165" by ICI | | |
| $C_{12}/C_{15}$ alkyl benzoate sold under the trademark "Finsolv TN" by Finetex | | 15% |
| ethylenediaminetetraacetic acid, sodium salt, $2H_2O$ | | |
| glycerol | | 0.1% |
| sorbitol | | 3% |
| crosslinked acrylic acid/($C_{10}$–$C_{30}$) alkyl acrylate copolymer sold under the trademark "Pemulen TR1" by Goodrich | | 2% |
| triethanolamine | | 0.5% |
| preservative | qs | 0.5% |
| demineralized water | qs | 100% |

Emulsion A (comparative) also comprises a 1,3,5-triazine derivative, which is 2,4,6-tris[p-(2'-ethylhexyl-1'-oxycarbonyl)anilino]-1,3,5-triazine (Uvinul T 150). Emulsion B, which is also comparative, contains Uvinul T 150 in combination with 4-tert-butyl-4'-methoxydibenzoylmethane (Parsol 1789). Emulsion C, according to the invention, comprises, besides Uvinul T 150 and Parsol 1789, ethyl N-butyl-N-acetylamino-propionate, sold under the trademark "R3535" by Merck.

The compositions of emulsions A, B and C are identified in Table (I) below (the amounts are expressed as a % by weight relative to the total weight of the composition):

TABLE (I)

| Compound | Emulsion A (comparative) | Emulsion B (comparative) | Emulsion C (invention) |
|---|---|---|---|
| Uvinul T 150 | 1.5% | 1.5% | 1.5% |
| Parsol 1789 | — | 0.5% | 0.5% |
| R3535 | — | — | 15% |

For each of these emulsions, the percentage of residual 2,4,6-tris[p-(2'-ethylhexyl-1'-oxycarbonyl)anilino]-1,3,5-triazine after UV irradiation was determined according to the following procedure: for each formula, four control samples and four test samples were prepared. 16 mg of formula were placed on frosted PMMA (polymethyl methacrylate) plates, which had been prerinsed with water and then dried, and the formula was spread over an area of 2 cm×4 cm. The plates were then irradiated (Suntest CPS Heraeus) for 4 hours in a chamber whose temperature is adjusted to about 35°–40° C. in order to simulate natural UV irradiation, while storing the control plates in darkness during the irradiation time of the other plates.

The samples were then analyzed in the following manner: the screening agents were extracted by immersing each plate in 55 ml of ethanol in order to dissolve the screening agents. The plates and the solvent containing the screening agents were then treated with ultrasound for 5 minutes in order to ensure efficient extraction. The solutions obtained are analyzed by high performance liquid chromatography.

For each formula tested, the level of residual 2,4,6-tris [p-(2'-ethylhexyl-1'-oxycarbonyl)anilino]-1,3,5-triazine after irradiation is given by the ratio of its concentration in the irradiated sample to its concentration in the non-irradiated sample.

The results, as a percentage of remaining 2,4,6-tris[p-(2'-ethylhexyl-1'-oxycarbonyl)anilino]-1,3,5-triazine, are collated in Table (II) below:

TABLE (II)

| Emulsion | Residual Uvinul T 150 |
| --- | --- |
| Emulsion A (comparative) | 93% |
| Emulsion B (comparative) | 69% |
| Emulsion C (invention) | 87% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective cosmetic composition suited for photoprotecting the skin and/or hair against the deleterious effects of UV radiation, comprising an effective amount of:

(i) at least one 1,3,5-triazine derivative having the structural formula (I):

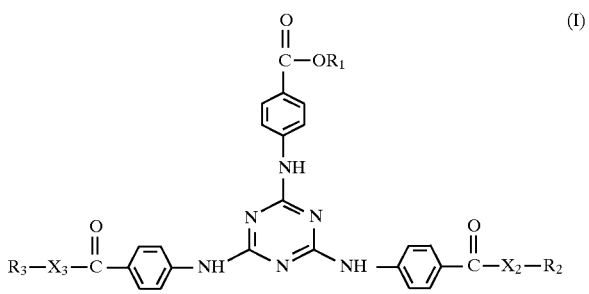

wherein:

$X_2$ and $X_3$, which may be identical or different, represent oxygen or an —NH— radical;

$R_1$, $R_2$ and $R_3$, which may be identical or different, are each hydrogen; an alkali metal; an ammonium radical optionally substituted with one or more alkyl or hydroxyalkyl radicals; a linear or branched $C_1-C_{18}$ alkyl radical; a $C_5-C_{12}$ cycloalkyl radical optionally substituted with one or more $C_1-C_4$ alkyl radicals; a polyoxyethylenated radical comprising from 1 to 6 ethylene oxide units and whose terminal OH group is methylated; or a radical of formulae (II), (III) or (IV) below:

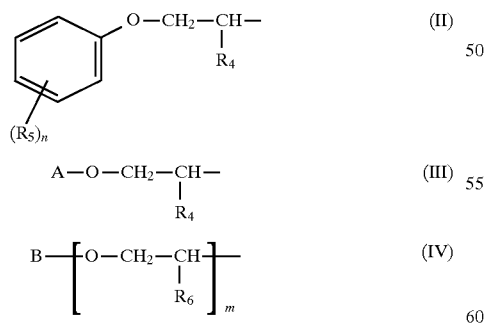

wherein:

$R_4$ is hydrogen or a methyl radical;
$R_5$ is a $C_1-C_9$ alkyl radical;
n is an integer ranging from 0 to 3;
m is an integer ranging from 1 to 10;
A is a $C_4-C_8$ alkyl radical or a $C_5-C_8$ cycloalkyl radical;

B is a linear or branched $C_1-C_8$ alkyl radical; a $C_5-C_8$ cycloalkyl radical; an aryl radical optionally substituted with one or more $C_1-C_4$ alkyl radicals;

$R_6$ is hydrogen or a methyl radical, (ii) at least one dibenzoylmethane derivative having the structural formula (V):

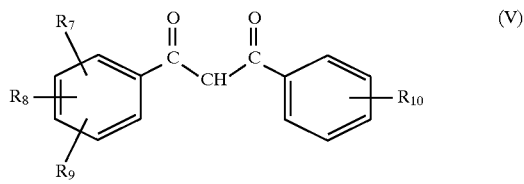

wherein $R_7$, $R_8$, $R_9$ and $R_{10}$, which may be identical or different, independently represent hydrogen or a hydroxyl radical or a linear or branched $C_1-C_8$ alkyl radical or a linear or branched $C_1-C_8$ alkoxy radical, and (iii) at least one amide compound, formulated into a topically applicable cosmetically acceptable vehicle, diluent or carrier therefor.

2. The photoprotective composition as defined by claim 1, wherein the 1,3,5-triazine derivative of formula (I) has the following substituents:

$X_2$ and $X_3$ are identical and represent oxygen;
$R_1$ is a $C_5-C_{12}$ cycloalkyl radical optionally substituted with one or more $C_1-C_4$ alkyl radicals; or a radical of formulae (II), (III) or (IV) wherein:
B is a $C_1-C_4$ alkyl radical;
$R_6$ is a methyl radical;
$R_2$ and $R_3$, which may be identical or different, are each hydrogen; an alkali metal; an ammonium radical optionally substituted with one or more alkyl or hydroxyalkyl radicals; a linear or branched $C_1-C_{18}$ alkyl radical; a $C_5-C_{12}$ cycloalkyl radical optionally substituted with one or more $C_1-C_4$ alkyl radicals; or a radical of formulae (II), (III) or (IV) wherein:
B is a $C_1-C_4$ alkyl radical; and
$R_6$ is a methyl radical.

3. The photoprotective composition as defined by claim 1, wherein the 1,3,5-triazine derivative of formula (I) has the following radicals:

$X_2$ and $X_3$ are identical and represent the —NH— radical;
$R_3$ is a linear or branched $C_1-C_{18}$ alkyl radical; a $C_5-C_{12}$ cycloalkyl radical optionally substituted with one or more $C_1-C_4$ alkyl radicals;
$R_1$ is hydrogen; an alkali metal; an ammonium radical; a radical of formula (IV); a linear or branched $C_1-C_{18}$ alkyl radical; or a $C_5-C_{12}$ cycloalkyl radical optionally substituted with one or more $C_1-C_4$ alkyl radicals; and
$R_2$ is a linear or branched $C_1-C_{18}$ alkyl radical; or a $C_5-C_{12}$ cycloalkyl radical optionally substituted with one or more $C_1-C_4$ alkyl radicals.

4. The photoprotective composition as defined by claim 1, wherein the 1,3,5-triazine derivative of formula (I) has the following substituents:

$X_2$ is oxygen;
$X_3$ is the —NH— radical;
$R_3$ is a linear or branched $C_1-C_{18}$ alkyl radical; or a $C_5-C_{12}$ cycloalkyl radical optionally substituted with one or more $C_1-C_4$ alkyl radicals;
$R_1$ is hydrogen; an alkali metal; an ammonium radical; a radical of formula (IV); a linear or branched $C_1-C_{18}$ alkyl radical; or a $C_5$–$C_{12}$ cycloalkyl radical optionally substituted with one or more $C_1$–$C_4$ alkyl radicals;

$R_2$ is hydrogen; an alkali metal; an ammonium radical; a radical of formula (IV); a linear or branched $C_1$–$C_{18}$ alkyl radical; or a $C_5$–$C_{12}$ cycloalkyl radical optionally substituted with one or more $C_1$–$C_4$ alkyl radicals.

5. The photoprotective composition as defined by claim 4, wherein the 1,3,5-triazine derivative corresponds to the following formula:

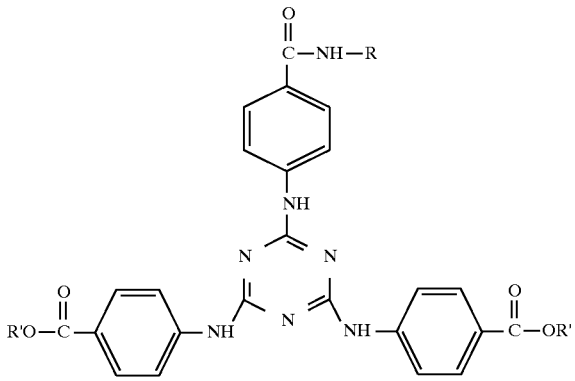

wherein R' represents a 2-ethylhexyl radical and R represents a tert-butyl radical.

6. The photoprotective composition as defined by claim 1, wherein the 1,3,5-triazine derivative has the following substituents:

$X_2$ and $X_3$ are identical and represent oxygen;

$R_1$, $R_2$ and $R_3$ are identical and represent a $C_6$–$C_{12}$ alkyl radical or a polyoxyethylenated radical comprising from 1 to 6 ethylene oxide units and in which the terminal OH group is methylated.

7. The photoprotective composition as defined by claim 6, wherein the 1,3,5-triazine derivative corresponds to the following formula:

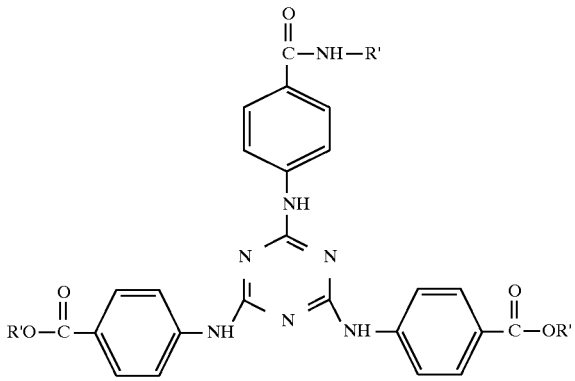

wherein R' represents a 2-ethylhexyl radical.

8. The photoprotective composition as defined by claim 1, wherein the 1,3,5-triazine derivative is present in the composition in an amount ranging from 0.5% to 20% by weight, relative to the total weight of the composition.

9. The photoprotective composition as defined by claim 8, wherein the 1,3,5-triazine derivative is present in an amount ranging from 1% to 10% by weight, relative to the total weight of the composition.

10. The photoprotective composition as defined by claim 1, wherein the dibenzoylmethane derivative comprises:

2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4-tert-butyl-4'-methoxydibenzoylmethane,
2-methyl-5-isopropyl-4'-methoxy-dibenzoylmethane,
2-methyl-5-tert-butyl-4'-methoxy-dibenzoylmethane,
2,4-dimethyl-4'-methoxydibenzoylmethane,
2,6-dimethyl-4-tert-butyl-4'-methoxydibenzoylmethane, or
4,4'-dimethoxydibenzoylmethane.

11. The photoprotective composition as defined by claim 1, wherein the dibenzoylmethane derivative is 4-tert-butyl-4'-methoxydibenzoylmethane.

12. The photoprotective composition as defined by claim 1, wherein the dibenzoylmethane derivative is present in the composition in an amount ranging from 0.2% to 15% by weight, relative to the total weight of the composition.

13. The photoprotective composition as defined by claim 12, wherein the dibenzoylmethane derivative from about 0.2% to 10% by weight, relative to the total weight of the composition.

14. The photoprotective composition as defined by claim 1, wherein the amide compound has the structural formula (VI):

wherein the radicals $R_{11}$, $R_{12}$ and R13, which may be identical or different, independently represent hydrogen or monovalent, saturated or unsaturated, aliphatic, cycloaliphatic or cyclic, optionally functionalized hydrocarbon radicals containing from 1 to 30 carbon atoms, inclusive, it being understood that, in this formula, the radical $R_{11}$ can form, with the radical $R_{12}$ or with the radical $R_{13}$, a ring containing from 5 to 18 carbon atoms, inclusively, and that the radicals $R_{12}$ and $R_{13}$ can together form a ring containing from 5 to 18 carbon atoms, inclusive.

15. The photoprotective composition as defined by claim 14, wherein the amide compound has at least one of the following characteristics:

the amide compound is an N-substituted amide, $R_{11}$ is a linear or branched, $C_1$–$C_{22}$ alkyl radical, or a phenyl radical which is itself optionally substituted with one or more linear or branched $C_1$–$C_{12}$ alkyl radicals, $R_{12}$ is a linear or branched, $C_1$–$C_{22}$ alkyl radical, $R_{13}$ is a linear or branched alkyl radical as defined for $R_{12}$, or R13 represents a monovalent radical with an ester function corresponding to structural formula (VII):

wherein $R_{14}$ and $R_{15}$, which may be identical or different, represent two hydrocarbon radicals, containing from 1 to 12 carbon atoms.

16. A photoprotective composition as defined by claim 15, wherein the amide compound has the following characteristics:

the amide compound is N,N-disubstituted, $R_{11}$ is a linear or branched $C_1$–$C_{22}$ alkyl radical, $R_{12}$ is a linear or branched, $C_1$–$C_{22}$ alkyl radical, and $R_{14}$ and $R_{15}$ represent an alkyl group having from 1 to 8 carbon atoms.

17. The photoprotective composition as defined by claim 1, wherein the amide compound is ethyl N-butyl-N-acetylaminopropionate.

18. The photoprotective composition as defined by claim 1, wherein the amide is present in the composition in an amount ranging from 0.01% to 50% by weight, relative to the total weight of the composition.

19. The photoprotective composition as defined by claim 18, wherein the amide ranges from 0.1% to 30% by weight relative to the total weight of the composition.

20. The photoprotective composition as defined by claim 1, wherein said composition is in the form of an oil-in-water emulsion.

21. A UV-protecting shape or article containing an effective UV-protecting amount of the composition as defined by claim 1.

22. A method for photoprotecting human skin and/or hair against the deleterious effects of UV irradiation, comprising topically applying thereto an effective UV-protecting amount of the photoprotective composition as defined by claim 1, to a patient in need thereof.

23. A method for controlling variation in skin color promoted by UV irradiation, comprising topically applying thereto an effective UV-screening amount of the composition as defined by claim 1, to a patient in need thereof.

24. A process for enhancing the stability to UV-irradiation of a photoprotective composition comprising a dibenzoylmethane derivative and a 1,3,5-triazine derivative, said process comprising introducing into said composition a stabilizing effective amount of an amide compound.

* * * * *